United States Patent
Hu et al.

(10) Patent No.: US 7,597,674 B2
(45) Date of Patent: Oct. 6, 2009

(54) VERSATILE ORTHOPAEDIC LEG MOUNTED WALKER

(75) Inventors: Irving Hu, Camarillo, CA (US); Chad Leeder, Newbury Park, CA (US); Tracy Grim, Thousand Oaks, CA (US)

(73) Assignee: Össur hf, Reykjavik (IS)

( * ) Notice: Subject to any disclaimer, the term of this patent is extended or adjusted under 35 U.S.C. 154(b) by 129 days.

(21) Appl. No.: 11/889,379

(22) Filed: Aug. 13, 2007

(65) Prior Publication Data

US 2007/0293798 A1 Dec. 20, 2007

Related U.S. Application Data

(63) Continuation-in-part of application No. 10/201,124, filed on Jul. 23, 2002, now Pat. No. 7,303,538.

(51) Int. Cl.
*A61F 5/00* (2006.01)
(52) U.S. Cl. .......................... 602/23; 602/27
(58) Field of Classification Search .............. 602/16, 602/20–23, 26–27; 128/882
See application file for complete search history.

(56) References Cited

U.S. PATENT DOCUMENTS

| | | | |
|---|---|---|---|
| 1,639,381 A | 8/1927 | Manelas | |
| 3,878,626 A | 4/1975 | Isman | |
| 4,267,650 A | 5/1981 | Bauer | |
| 4,771,768 A | 9/1988 | Crispin | |
| 4,974,583 A | 12/1990 | Freitas | |
| 5,078,128 A | 1/1992 | Grim et al. | |
| 5,250,021 A | 10/1993 | Chang | |
| 5,329,705 A | 7/1994 | Grim et al. | |
| 5,355,562 A | 10/1994 | Matoba et al. | |
| 5,368,551 A * | 11/1994 | Zuckerman | 602/23 |
| 5,452,527 A | 9/1995 | Gaylord | |
| 5,464,385 A | 11/1995 | Grim | |
| 5,546,642 A | 8/1996 | Anscher | |
| 5,713,837 A * | 2/1998 | Grim et al. | 602/6 |
| 5,716,335 A * | 2/1998 | Iglesias et al. | 602/27 |
| 5,983,528 A | 11/1999 | Hartung | |
| 6,102,881 A | 8/2000 | Quackenbush et al. | |
| 6,155,998 A | 12/2000 | Gilmour | |
| 6,299,588 B1 | 10/2001 | Fratrick | |
| 6,345,454 B1 | 2/2002 | Cotton | |

FOREIGN PATENT DOCUMENTS

DE 2651089 5/1978

* cited by examiner

*Primary Examiner*—Michael A. Brown
(74) *Attorney, Agent, or Firm*—Bacon & Thomas, PLLC

(57) ABSTRACT

An orthopedic walker for mounting on the lower leg of a patient includes a walker base having a central area for receiving the foot of a patient and a spaced lower surface including an outer sole, and a pair of struts connected to the walker base. Each of the struts has a frame member of high strength material secured to the first end of the walker base and a supporting component integrally secured and adjacent to the frame member. The supporting component defines laterally extending side wings generally corresponding to the second end of the frame member, and is constructed from a material less rigid than the high strength material of the frame member. The supporting component has a main body and a border portion that are integrally secured and contiguous with one another. The border portion is formed from a material having a lower hardness than the material forming the main body.

23 Claims, 17 Drawing Sheets

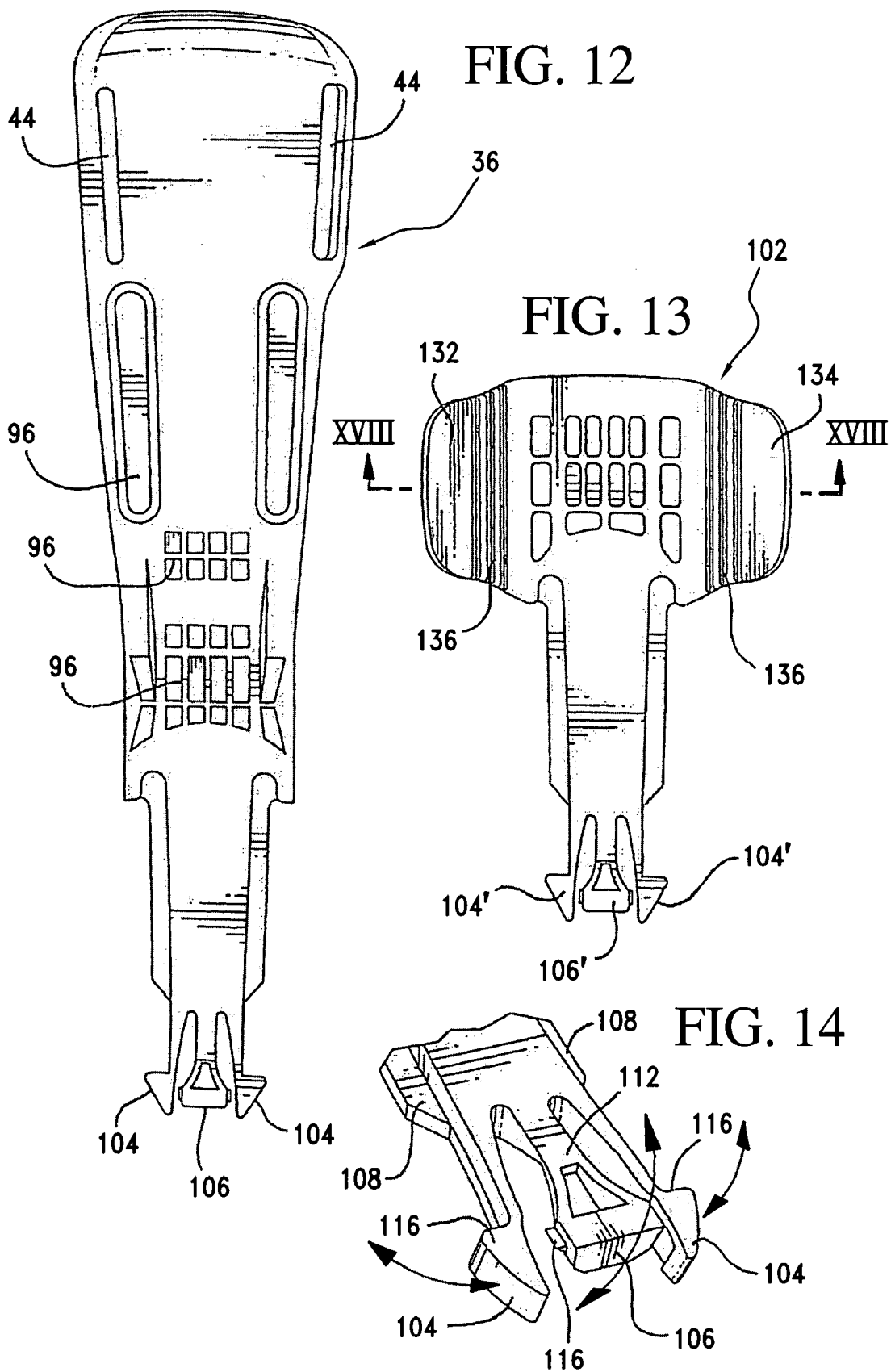

VERSATILE ORTHOPAEDIC LEG MOUNTED WALKER

CROSS REFERENCE TO RELATED APPLICATIONS

This application is a continuation-in-part of U.S. application Ser. No. 10/201,124 filed on Jul. 23, 2002.

FIELD OF THE INVENTION

This invention relates to orthopaedic walkers, which are orthopaedic support boots which encompass the foot, ankle and lower legs, for use by persons recovering from injuries such as broken bones or other trauma of the lower leg, ankle or foot. This type of orthopaedic product is often referred to as a "short leg walker."

BACKGROUND

Leg mounted orthopaedic walkers are well known, and typical patents disclosing such walkers include the following:

U.S. Pat. No. 4,771,768 Granted: Sep. 20, 1988 Inventor: Crispin Title: Controlled Motion Ankle Fracture Walker.

U.S. Pat. No. 5,078,128 Granted: Jan. 7, 1992 Inventor: Grim et al. Title: Removable Leg Walker.

U.S. Pat. No. 5,329,705 Granted: Jul. 19, 1994 Inventor: Grim et al. Title: Footgear with Pressure Relief Zones.

U.S. Pat. No. 5,368,5581 Granted: Nov. 29, 1994 Inventor: Zuckerman Title: Ankle Brace Walker.

U.S. Pat. No. 5,464,385 Granted: Nov. 7, 1995 Inventor: Grim Title: Walker with Open Heel.

In order to maximize its effect and provide comfortable wear to the user of the walker, it is desirable that a walker securely and precisely fit the leg of the wearer. While walkers are made to generally conform to the geometry of a leg of a wearer, it is common for the geometry of the leg to change thereby requiring the walker to accommodate a variety of geometries of the leg.

A common feature with many conventional walkers is a pair of struts formed from a high strength material that is used as a frame upon which circumferential straps are secured. A softgood support is also used so as to be wrapped about the leg, foot and ankle, and contained within the struts. The straps are typically secured to the struts via corresponding hook and loop fastening material, and are further accompanied with D-rings to allow for tensioning of the straps relative to the struts.

A frequent problem with these conventional struts is that the edges of the struts are hard and unforgiving against the leg of the patient even with the softgood support surrounds the leg. This leads to undesirable pressure points, a deterioration of the softgood support, and an overall dissatisfaction and discomfort to the patient. As a result, many patients jettison the walkers prior to full healing of the leg, foot or ankle, and thus fail to comply with the walker wear instructions.

Additional shortcomings are readily found in conventional braces such that the struts (1) may not include readily interchangeable long and short struts; (2); they may not readily accommodate different sized lower legs; (3) the mechanisms for securing the struts to the base may be either permanent, or subject to failure; (4) the flexibility of the struts may be substantially linear, and therefore may be too flexible throughout bending cycles to provide adequate orthopaedic support, or may be unduly stiff so as to irritate the user.

In recognizing the need for effective walkers, various walkers have been introduced into the marketplace. Such walkers, however, have generally comprised relatively heavy, bulky apparatuses that fail to provide ventilation and evenly distribute pressure from the walker on the leg of the wearer. Moreover, many contemporary walkers are deficient in that the walkers are constructed in a manner that do not consistently provide or lack adjustment features for forming a firm and secure interface between the leg and knee of the wearer and the walkers. As a result of these drawbacks, many walkers detract from the user's endeavor.

The features of the present invention are provided in recognition of the need for walkers that achieve acceptable function performance characteristics while being comfortable to the wearer when worn. This recognition is realized with the invention described hereinafter.

SUMMARY

In accordance with one specific illustrative embodiment of the invention, a versatile walker which overcomes the shortcomings outlined hereinabove may include at least one of the following features:

1. The struts are secured to the base on a snap-in basis using a three pronged extension on the lower end of the struts, with the two outer prongs constituting locking members which fit into grooves and recesses in the base, with the third, central prong being resiliently biased toward the outer prongs so that when the two outer prongs lock into place, the central prong blocks their release.

2. Both long struts and short struts are provided, with identical locking arrangements on their lower ends, which may be of the type as outlined hereinabove.

3. The struts may be provided with reduced thickness zones to increase flexibility and to accommodate different anatomical configurations without sacrificing stability. Reduced thickness zones located below the upper end of the struts but at least an inch or two above the ankle joint can provide medial/lateral flexibility or hinge points to accommodate patients with relatively large lower legs. It is also noted that the medial/lateral hinge action may be provided by physical hinges or pivot points along the length of the strut, rather than by reduced strut thickness.

4. The struts may be provided either at the juncture with the base or along their length, with variable resiliency mechanisms, to permit initial easy deflection to accommodate minor deflections of the struts, and with arrangements for increasing resistance to deflections greater than a predetermined distance or angle. These arrangements may include reduced thickness in the struts, and a stop which is engaged when the deflection exceeds a predetermined amount.

5. The struts may have outwardly extending flaps or wings which may be hingedly secured to the central part of the strut, to accommodate various sizes of the patients' anatomies. So called "living hinges," or lines of reduced thickness, or grooves, extending partially through the plastic strut, may be employed to provide the hinging function.

6. The outer sole or outsole of the walker may include protrusions which may be hollow or doughnut shaped, in its upper surface to provide resiliency and cushioning during walking. And the outsole may extend upward around the outer periphery of the base, and have a peripheral bead interfitting with a mating recess in the base and providing a continuous smooth exterior surface at the junction between the outsole and the base. The base may be cored from the sides at the central area of the walker, and may be cored with relative small recesses from the top, toward the front and rear of the base, to reduce the weight of the walker. The outsole extends over the side core openings, thereby preventing the entry of foreign material, and provides a pleasing aesthetic appearance.

7. The strap retention loops or D-rings which are employed for pivoting functions are formed of one piece moldings, with the integral pivot pin pivotally locking the D-ring onto the plastic walker base.

It is to be understood that all of the foregoing features contribute to the realization of versatile walkers in which either long or short struts may be employed and which accommodate patients with different types of injuries, and patients with different anatomical configurations.

It is further noted that in some cases, instead of having separate struts secured to a base, the struts may be integrally molded with the base.

Advantages of the walker designs described herein include the elimination of decorative side caps, increased outsole adhesion to the plastic base, resistance to water, mud and dirt, increased surface contact and gripping action, increased resiliency between outsole and plastic base and improved aesthetic appearance resulting from the smooth outer surface mating of the outsole and the plastic base. The upward extent of the oustsole of the base, and the interfitting recess and groove also prevents delamination of the outsole from the base. Variations in the size of the ankles and lower leg are accommodated by living hinges and by increased flexibility within preset angular limits. Safety is assured by the triple locking mating arrangements between the struts and plastic base. Costs are reduced by the use of integrally molded D-rings which may provide pivoting action, by the simplification of the walker structure, and by avoiding the need for different walker configurations for different anatomical configurations.

In accordance with another embodiment described and illustrated herein, an improved walker provides a strut having a frame member that is over-molded with a supporting component possessing discrete regions having superior pressure-relieving properties. The first end of the frame member is releasably secured to the first side of a base member carrying the sole. The supporting component is integrally secured to and contiguous with the second end of the frame member. The supporting component is contiguous with the frame member in a manner that results in it directly touching the frame member so as to effectively be continuous therewith out any intermediate adhesive or substrate. Preferably, the supporting component interlocks with the frame member wherein the material of the supporting component is molded into recesses or apertures of the frame member.

According to one variation of this embodiment, the supporting component defines a border portion that is generally located along at least a segment of a peripheral edge of the supporting component, and a main body generally adjacent to the frame member. The border portion is characterized as a pressure-relieving edge portion that may have lower hardness properties than hardness properties of the main body. The border portion is preferably integrally molded with the main body in a manner that material of the border portion directly interlocks with the main body and is contiguous therewith.

The supporting component may include a variety of features in addition to the main body/border portion configuration, such as openings for providing ventilation and weight reduction, and a living hinge in the form of areas of the supporting component of reduced thickness so as to facilitate bending of the supporting component. In another variation of the supporting component, generally vertical elongate slots are formed on the main body to accommodate a strap. The elongate slots may include an overmolded feature provided about the periphery of the slot formed by the main body and the overmolded features may comprise a material that is generally harder or wear resistant than the material of the main body. In yet another embodiment, recesses may be formed about portions of the main body to accommodate padding material, and hook and loop material to thereby hold the materials in a manner to conceal or streamline the attachment of such materials to the strut.

Other objects, features and advantage will become apparent from a consideration of the following detailed description, and from the accompanying drawings.

BRIEF DESCRIPTION OF THE DRAWINGS

FIG. 12 is a side view of a long strut shown separate from the complete walker.

FIG. 13 is a view from the inside of a short strut which may be employed when the injury is confined to the ankle or lower ends of the lower leg bones.

FIG. 14 is a perspective view of the three prong locking mechanism for the struts.

DETAILED DESCRIPTION OF THE PREFERRED EMBODIMENTS

Figure 1:
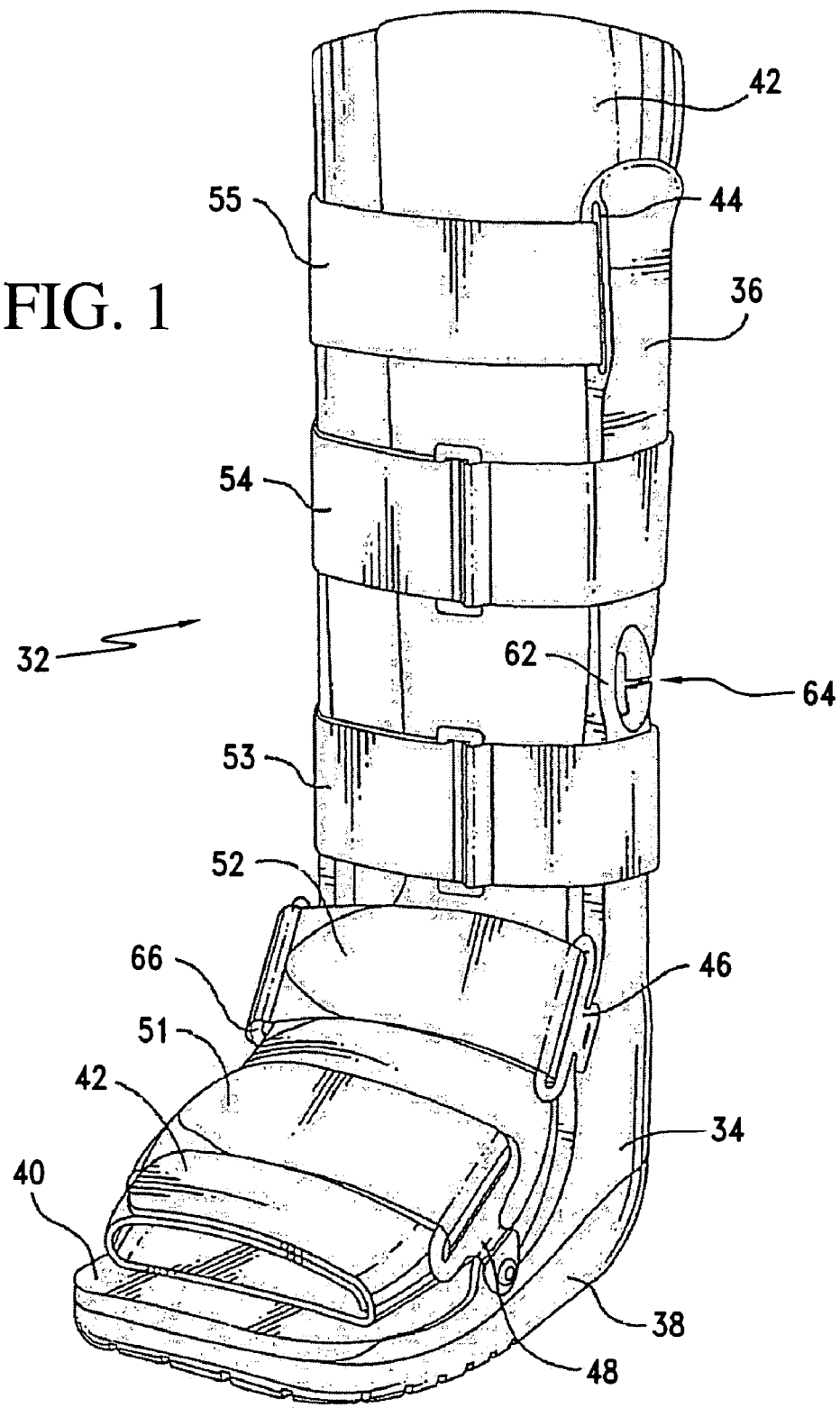
FIG. 1 is a perspective view of an orthopaedic walker illustrating the principles of the invention.
Figure 2:
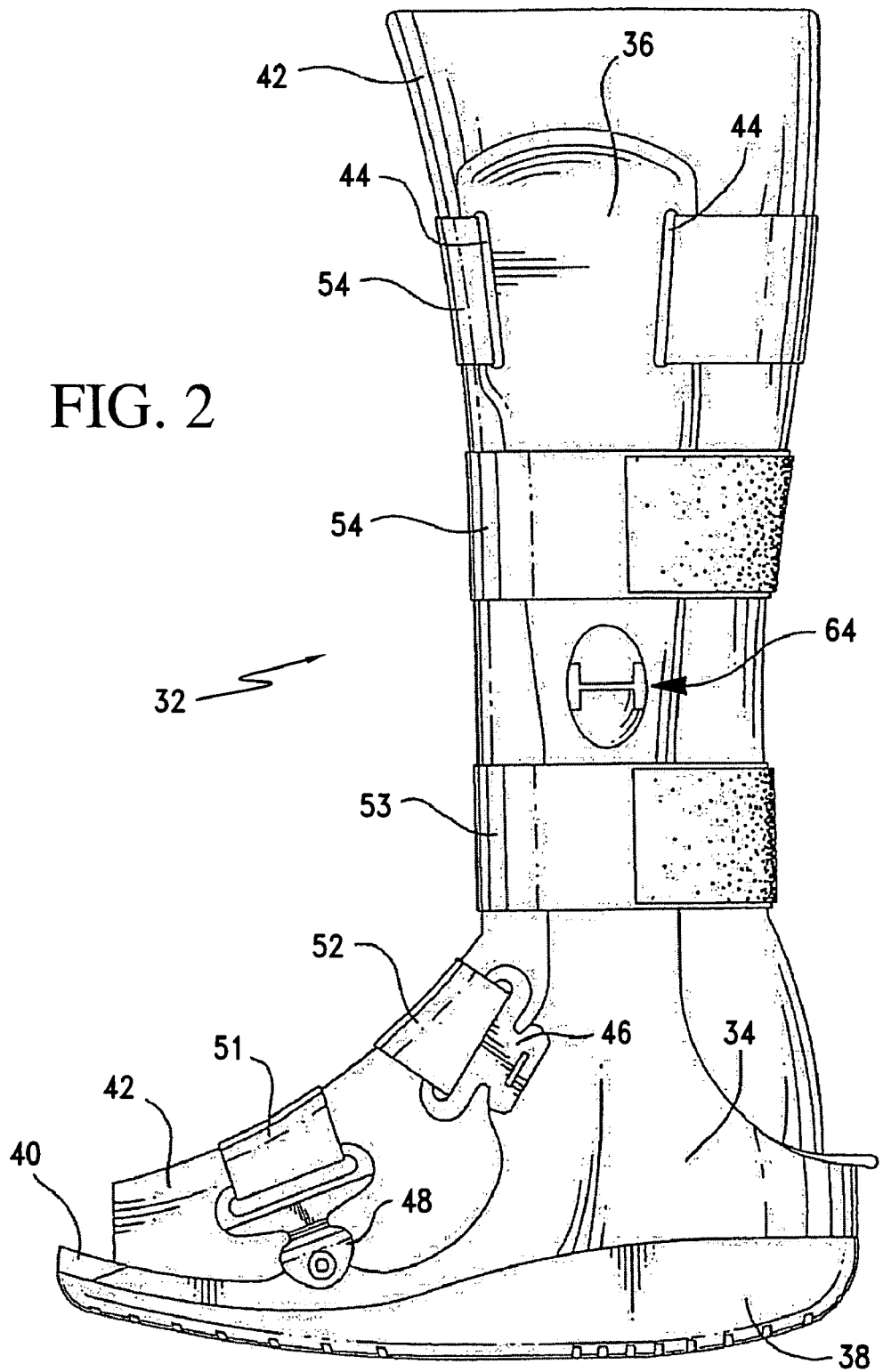
FIG. 2 is a left side elevational view of the walker of FIG. 1.

Referring more particularly to the drawings, FIG. 1 is a perspective view of a walker 32 illustrating the principles of the invention. The walker of FIG. 1 includes an engineered plastic base member 34, two struts, one of which is visible at reference 36, and an outersole, or outsole 38. The plastic base 34 may, for example be formed of glass fiber filled nylon, but other high strength plastics or other materials may be employed such as aluminum which may for example be powder coated. A resilient layer 40, which may be formed of one-quarter inch thick resilient foam, provides a cushion between the foot and the upper surface of the plastic base 34.

Additional padding 42 extends around the foot, ankle and lower leg of the patient. The padding 42 is held in place between the struts including strut 36 by hook and loop material of the VELCRO type, with hook type material extending along the inner surface of the struts, and with the padding 42 either having mating loop material on its outer surface, or being of a type of fabric which will inherently mate with hook type material.

It may be noted in passing that FIGS. 1 through 6 of the drawings are substantially the same as the first six figures of a design patent application filed on Jul. 23, 2002, and entitled "Top and Sides of Resilient Orthopaedic Walker".

Continuing with the description of FIG. 1 of the drawings, the straps 51 through 55 extend around the padded foot, ankle and lower leg of the patient. They are secured to the base 34 and the struts by slots such as slot 44 in strut 36 or by D-rings, such as D-ring 46 or pivoted D-ring 48. The straps are provided with mating hook and loop material on their overlapping surfaces so that they are readily adjustable. The integrally formed D-ring 48 will be discussed in greater detail hereinbelow.

The strut 36 is reduced in thickness in the area 62 to increase the flexibility of the strut, to readily accommodate patients with large lower legs. However, to insure orthopaedic stability and support, a stop mechanism 64 is provided. As disclosed in greater detail hereinbelow (see FIG. 17), the stop mechanism 64 has two surfaces spaced apart by a narrow space. Accordingly, as the walker is being fitted to a person with a large lower leg, the upper portion of the strut 36 may easily flex outward. However, if in use, the strut 36 is flexed beyond a predetermined distance or angle, preferably at least equal to 15 degrees but less than 30 degrees, the two spaced surfaces at reference numeral 64 engage, and there is much higher resistance against further deflection, and increased support for the leg.

Concerning the straps 51 and 52, they each have one end permanently secured to a D-ring, with the D-ring 66 for strap 52 being visible. The free ends of straps 51 and 52 pass through D-rings 48 and 46, respectively and then fold back and engage facing surfaces of the straps by hook and loop securing material. The other straps 53, 54 and 55 similarly extend around the assemblies in a generally conventional manner with slots in the struts and/or hook and loop material on the outer surfaces of the struts holding the straps in place.

Figure 7:
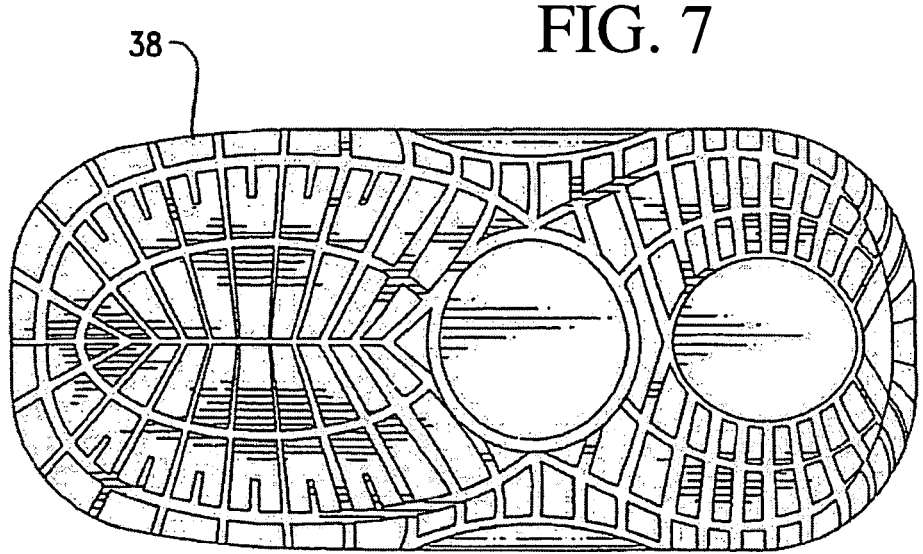

FIGS. 2 through 7 are various views of the walker as shown in FIG. 1, with FIG. 7 showing the patterned bottom layer of the outer sole, or outsole 38 for increased friction and traction. The outsole is bonded to the plastic base 34 by adhesive, and the outsole extends around and up the sides of the plastic base.

Figure 8:
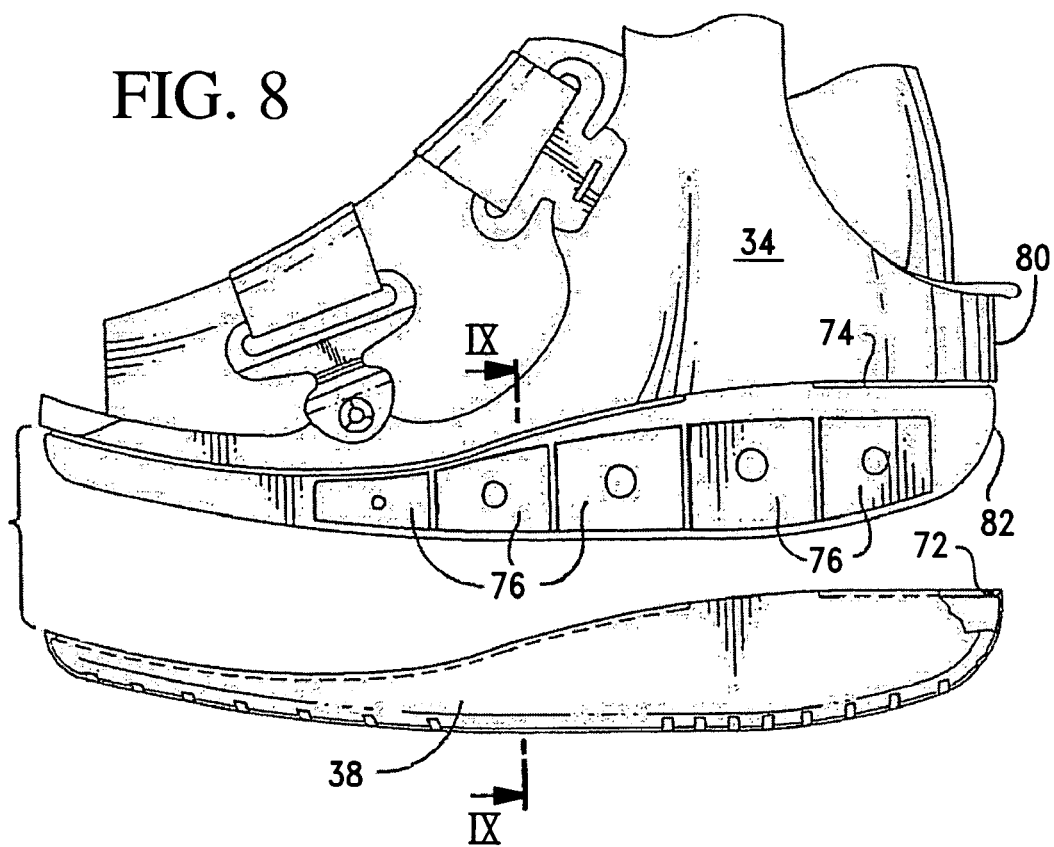
FIG. 8 is a partial exploded side view of the walker with the outer sole, or outsole spaced from the walker base.
Figure 9:
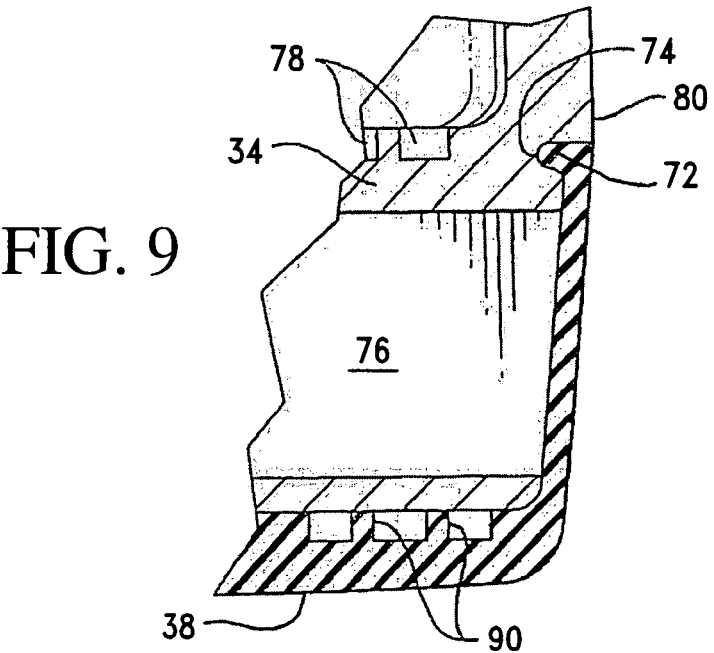
FIG. 9 is a partial cross sectional view along line IX-IX in FIG. 8 showing the smooth interfit between the walker base and the outsole.

As shown to advantage in FIGS. 8 and 9 of the drawings, the upper edge of the outsole 38 has a ridge 72 which interlocks with a mating peripheral recess 74 in the base. This configuration increases traction and resists delamination of the outsole from the base. Instead of the simple ridge and groove as shown, more complex interlocking structures may be employed; and the ridge and groove may be reversed.

Referring to FIGS. 8 and 9 of the drawings, the cored openings 76 which extend inwardly to a thin central web, and the cores 78, are clearly shown. Referring back to FIGS. 1, 2 and 4 of the drawings, note that the outsole 38 covers the entry to the cored openings 76. This has the advantage of preventing ingress of mud or other foreign material.

It may also be noted that the outward extent of the walker base 34 in the area 80 just above the peripheral recess 74 is greater than the outward extent in area 82 just below recess 74, by a predetermined thickness equal to the thickness of the outsole 38. This configuration presents a smooth exterior in the area where the outsole 38 mates with the base 34; and has the advantages of avoiding protrusions which might catch on objects as the patient walks and also presents a pleasing aesthetic appearance. It also avoids the need for additional components for closing the ends of the cored areas 76.

Figure 10:
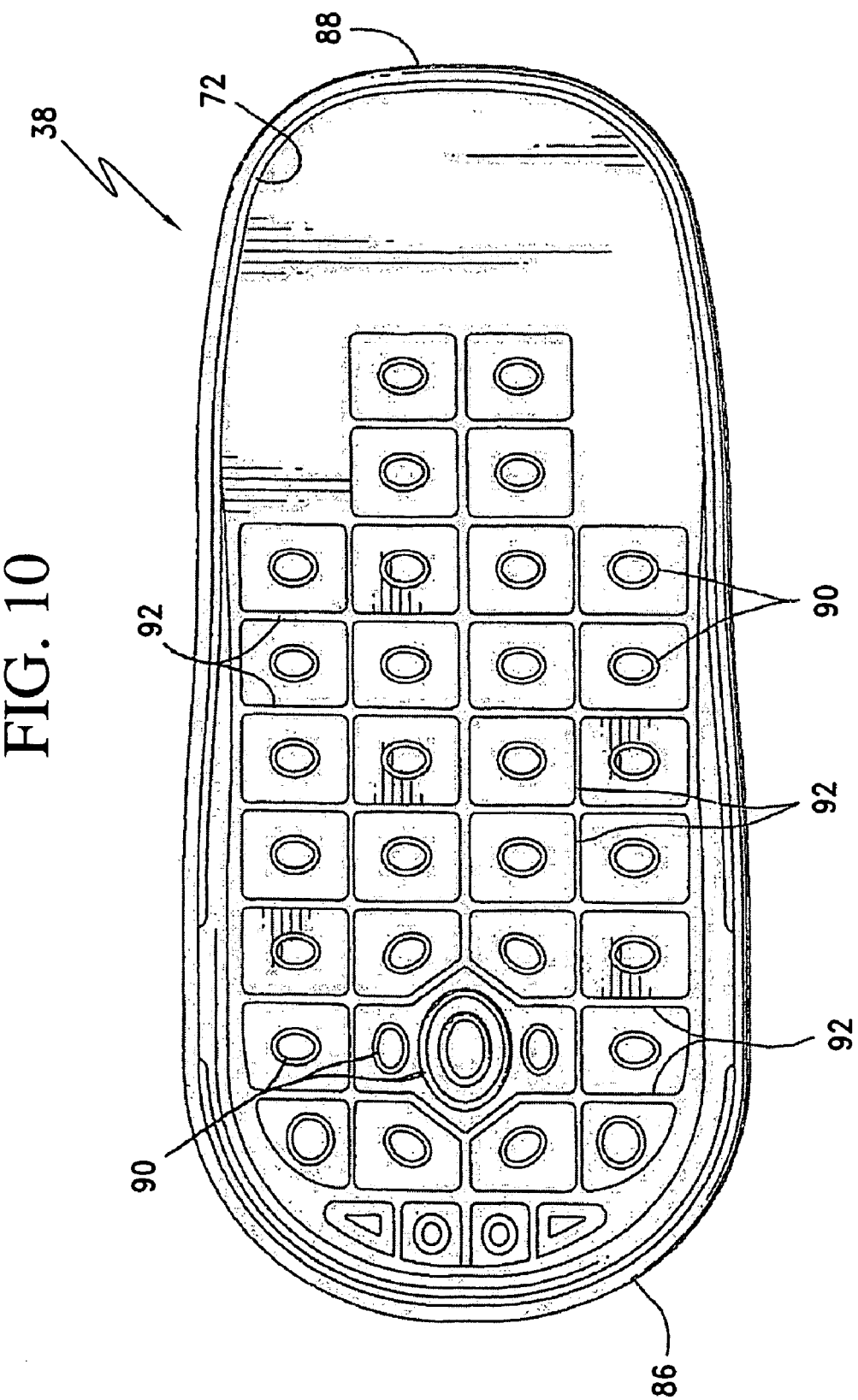
FIG. 10 is a top plan view of the outsole.

FIG. 10 is a top plan view of the outsole 38 with the heel area to the left as shown in FIG. 10 and the toe area to the right. This is a view of the inside of the outsole 38, and includes a large number of hollow doughnut shaped protrusions 90, and upwardly extending walls or ridges 92. These protrusions and walls extend upwardly from the continuous underlying surface of the outsole 38; and they provide additional resiliency particularly in the heel area, where the heel strike portion of a walking stride could otherwise provide a shock to the injured lower leg or foot of the patient. It is also noted that the closed wall protrusions trap air between the lower portion of the outsole and the mating surface of the base 34, thereby increasing the resiliency and buoyancy provided by the outsole. It is also noted that the outsole 38 is preferably adhesively bonded to the base 34.

Figure 11:
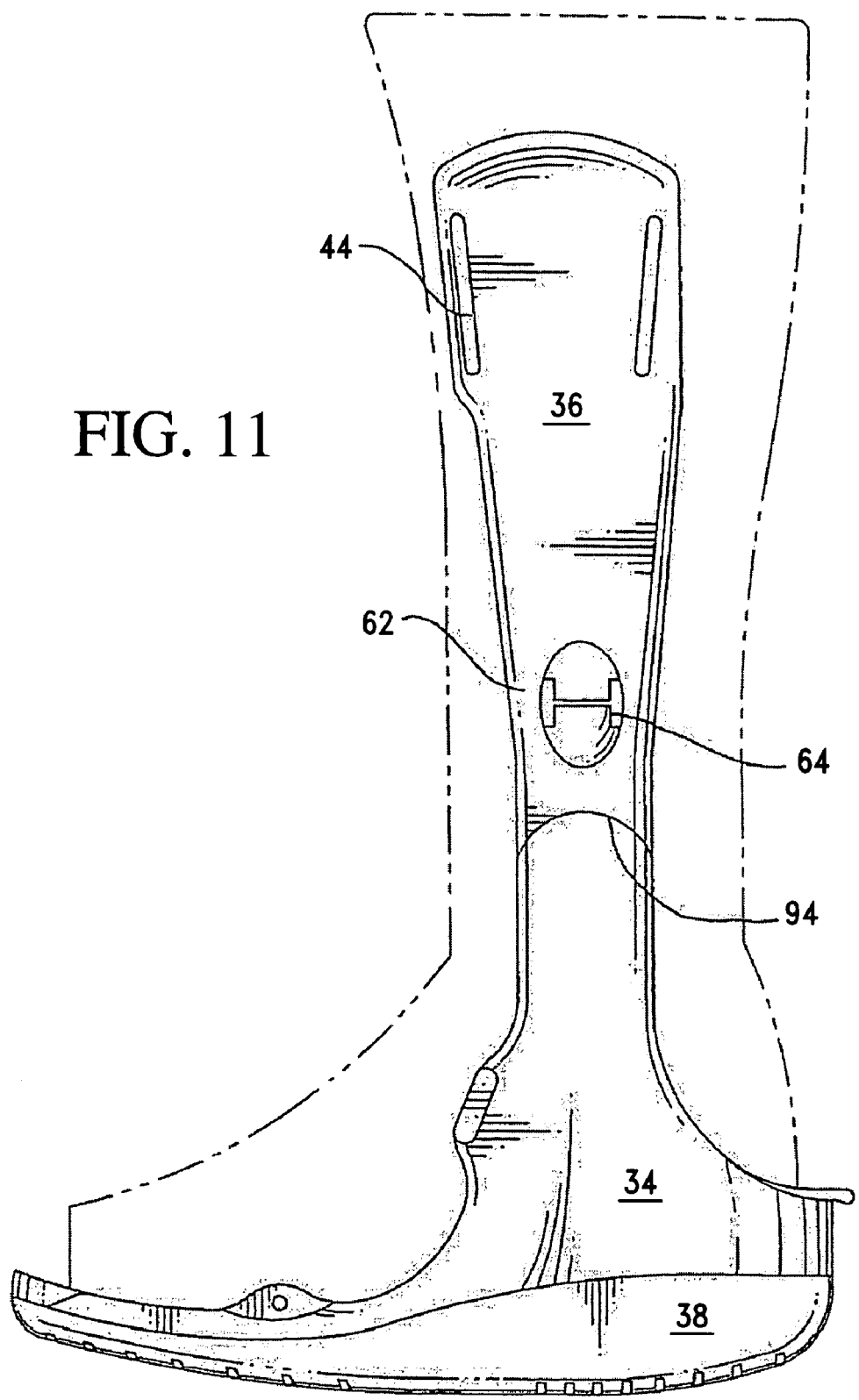
FIG. 11 is a side elevational view of the walker with the straps, D-rings and padding removed.

FIG. 11 is a side view of the walker of FIG. 1 with the padding straps and D-rings removed. Apart from matters previously mentioned, the line 94 represents the mating surfaces between the strut 36 and the walker base 34.

FIG. 12 is a plan view of the inside of a long strut which is, by way of example and not of limitation, about 13 inches long. It includes openings or slots 44, and recesses 96 to reduce the weight of the assembly. As indicated in earlier figures of the drawings, the slots 44 receive straps, such as strap 55 for holding the walker securely onto the patient.

The short strut 102 shown in FIG. 13 of the drawings is about 6½ inches long, and, with its laterally extending wings 132 and 134, is about 4½ inches wide.

The lower end of the long strut 36 has a triple locking mechanism including three prongs, the two outer prongs 104, and a central locking prong 106. The short strut 102 has an identical three prong locking mechanism including the two outer prongs 104' and the central locking prong 106'.

Figure 15:
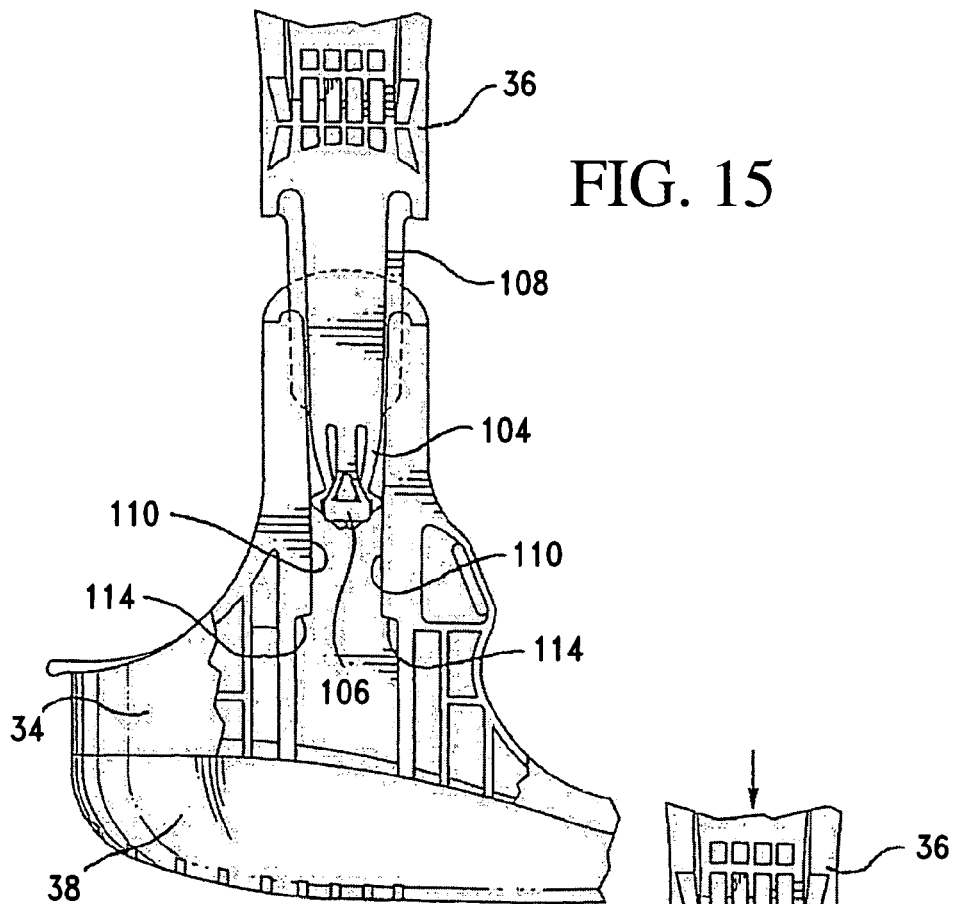
FIG. 15 is a fragmentary assembly drawing showing the strut partially assembled to the base.

FIG. 14 is a perspective view of the locking mechanism at the lower end of the struts. Note that, in addition to the three locking prongs, 104, 106, the struts have two thin outwardly extending longitudinal flanges 108 which mate with the longitudinal grooves or slots 110 on the strut support (see FIG. 15). Incidentally, it may be noted from FIG. 14 that the prongs 104,106 are thicker than the flanges 108, so that, as shown in FIG. 15, the ends of the prongs 104 do not slide in the grooves or slots 110, but ride on the outer edges of these slots 110. Incidentally the central portion 112 of the central locking prong 106 is of significantly reduced thickness, so that it may readily bend in the direction perpendicular to the plane of the strut, as indicated by arrow 114 in FIG. 14.

FIG. 15 shows the strut 36 partially assembled into the base 34, with the flanges 108 mating with slots or grooves 110. The outer prongs 104 are severely bent inward, and the central locking prong 106 is bent up out of the plane of the paper. The locking shoulders 114 are available to receive the outwardly extending surfaces 116 of the outer prongs 106 (see FIG. 14).

Figure 16:
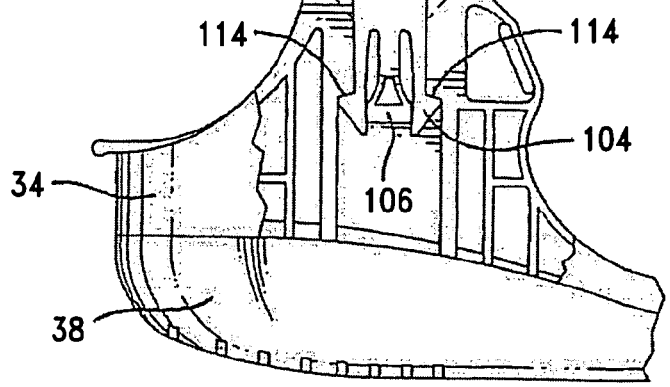
FIG. 16 is similar to FIG. 15 but shows the strut locking mechanism fully assembled and locked.

The fully locked position of the strut 36 is shown in FIG. 16, with the prongs 104 having surfaces 116 locked over the locking shoulders 114. The final locking step is accomplished by pressing the central locking prong 106 firmly into the space between the outer prongs 104 so that its outwardly extending protrusions 116 (see FIG. 14) interlock with recesses on the facing surfaces of the outer prongs 104.

As noted above, with both the long and the short walkers having identical locking mechanisms, a walker of either type may be formed using a common base, and the desired long or short struts.

Figure 3:
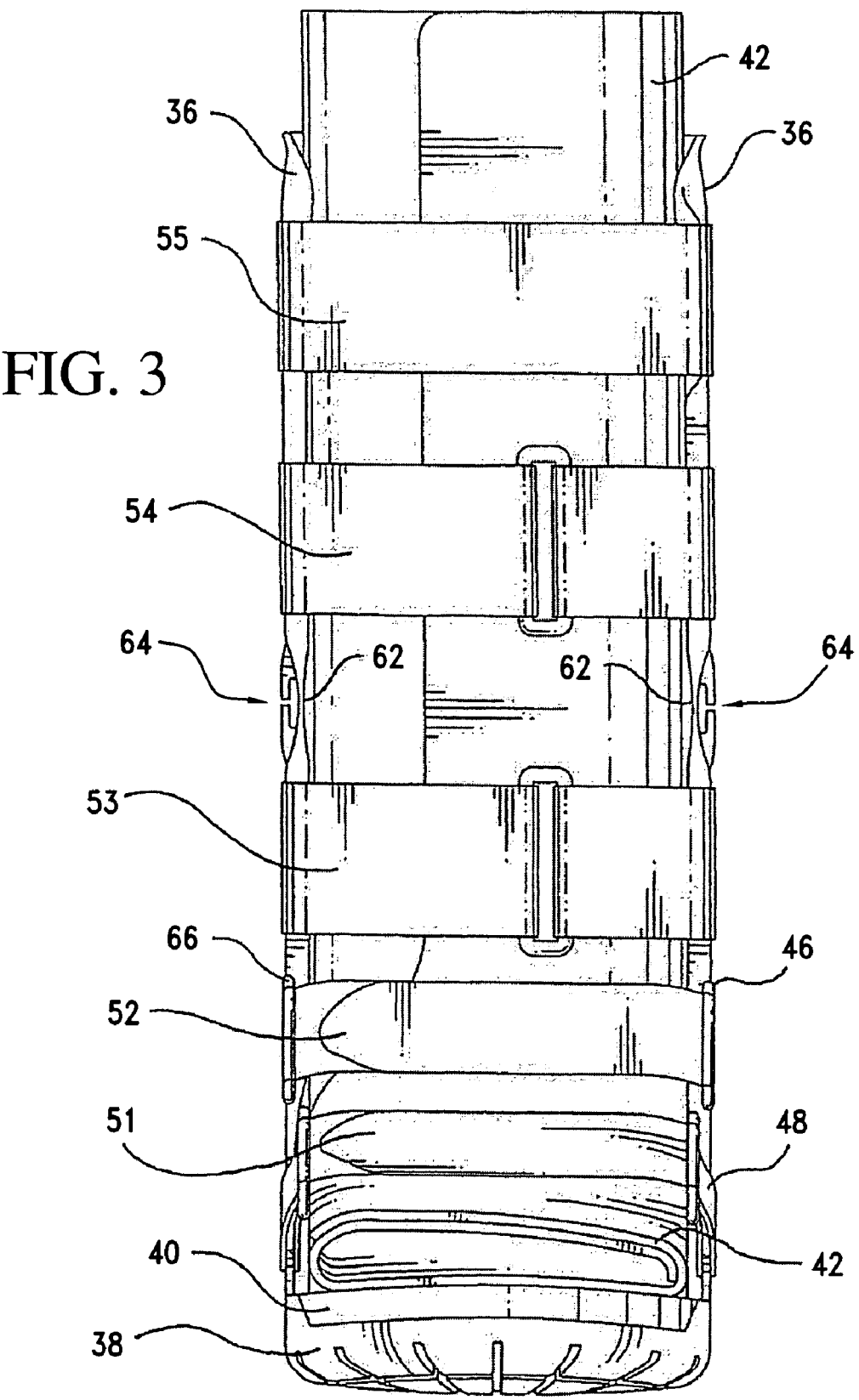
FIG. 3 is a front elevational view of the walker of FIG. 1.
Figure 4:
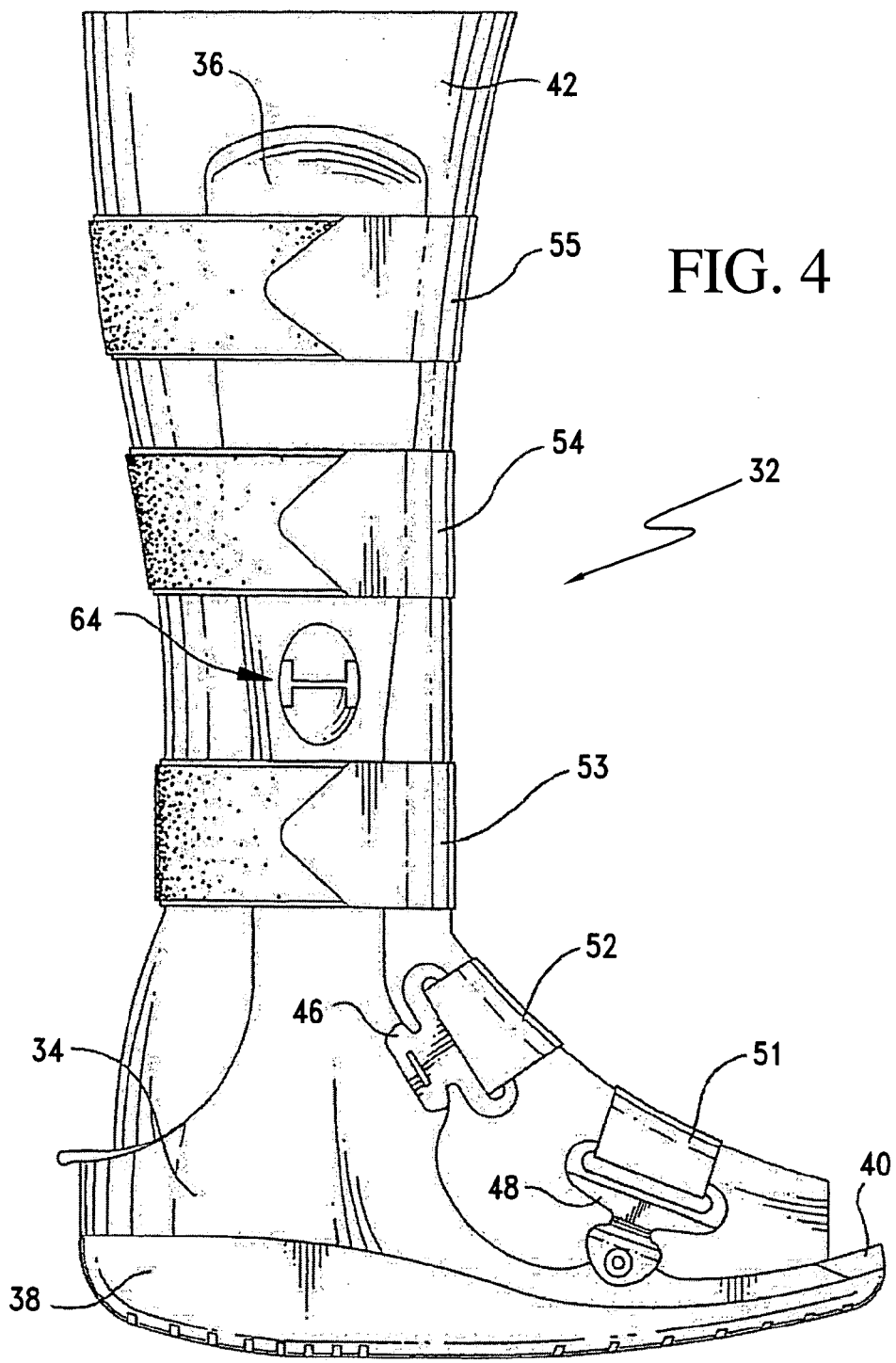
FIG. 4 is a right side elevational view of the walker of FIG. 1.
Figure 5:
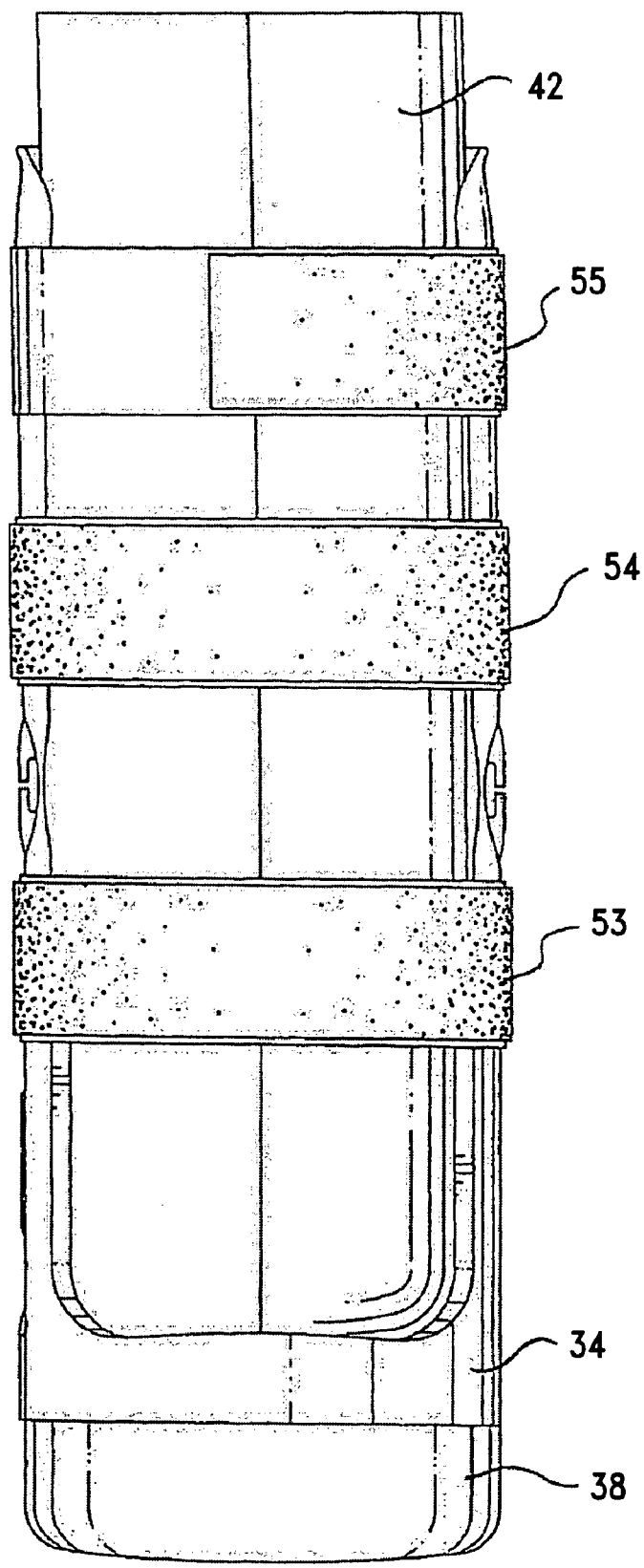
FIG. 5 is a rear elevational view of the walker of FIG. 1.
Figure 6:
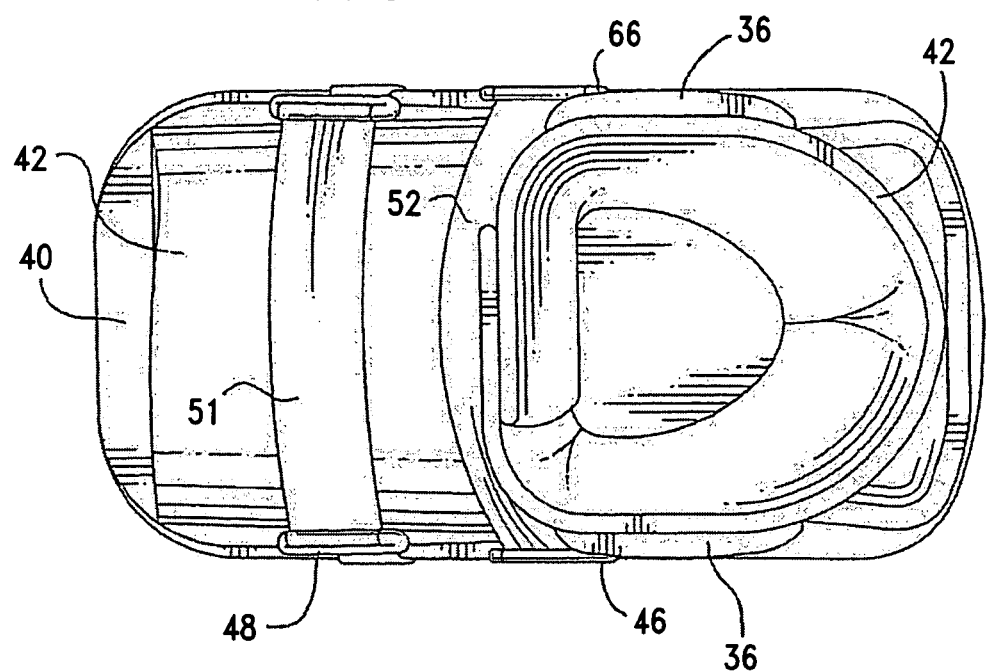
FIGS. 6 and 7 are top and bottom plan views of the walker.
Figure 17:
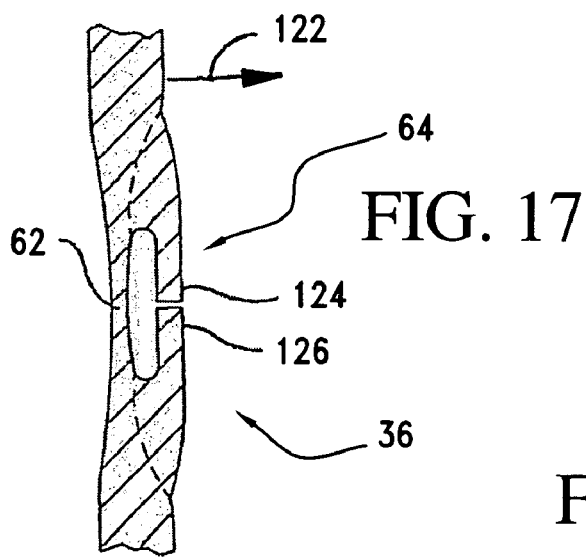
FIG. 17 is a partial cross-sectional view of one of the long struts showing the reduced cross-section, for increased flexibility and the limiting stop arrangements.

Attention is now directed to FIG. 17 which should be considered along with FIGS. 3 and 11 of the drawings. As mentioned above, the struts such as strut 36 may be thinned down in area 62, to increase flexibility to readily accommodate patients with varying size lower legs. However, following deflection in the direction indicated by arrow 122, the surfaces 124, 126 engage, and provide the desired orthopaedic structural support. This combination of initial flexibility and subsequent increased stiffness and reduced flexibility both accommodate varying size lower legs, and also provides the desired orthopaedic support.

Figure 18:
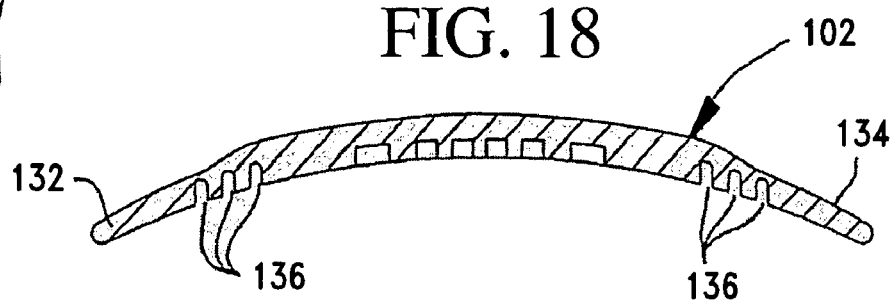
FIG. 18 is a transverse cross-section along line XVIII-XVIII in FIG. 13 of one of the shorter struts showing the hinge lines of flexibility.

Referring now to the short walker strut of FIG. 13 and the cross-sectional view of FIG. 18, taken along plane XVIII-XVIII of FIG. 13, the short strut 102 is provided with laterally extending wings 132 and 134, with vertically extending lines of weakness or so-called "living hinges" 136. In practice two struts such as strut 102 are mounted on a walker base, with padding around the ankle of the type shown in FIGS. 1-6, but somewhat shorter, commensurate with the height of the struts. Straps are mounted to the struts and to the padding preferably using the hook and loop principle; and the wings 132, 134 on the short struts, are flexed to make a close supporting fit with the size of the foot and ankle of the patient.

Figure 19:
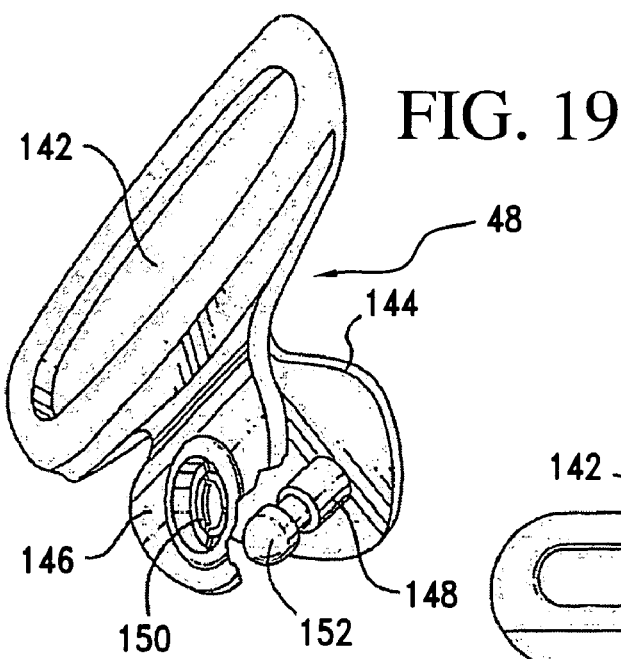
FIG. 19 is a perspective view of an integral pivotal "D-ring."
Figure 20:
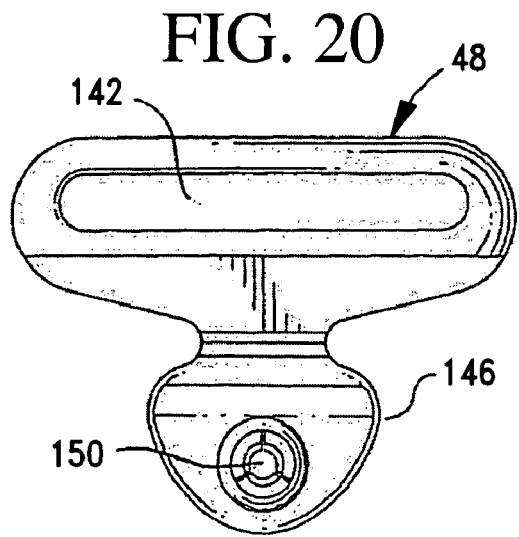
FIG. 20 is a partial elevational view of the D-ring of FIG. 19.

FIGS. 19 and 20 relate to the integrally molded pivotal D-ring of the type shown at 48 in FIG. 1 of the drawings. In FIG. 19, the "D-ring" 48 has an opening 142 for receiving a strap, and two integrally molded flaps 144 and 146. The flap 144 has an integrally molded pivot pin 148 formed thereon; and the flap 146 has a variable size opening 150. As indicated in FIG. 20 the opening 150 has outwardly directed cuts so that the rounded head 152 of pin 148 can snap through the hole. The side walls of the hole will then snap back and engage the reduced diameter section of the pin and retain the pin in its closed position, normally locked into a hole in an orthopaedic walker or support as indicated in FIG. 1 of the drawings.

Figure 21:
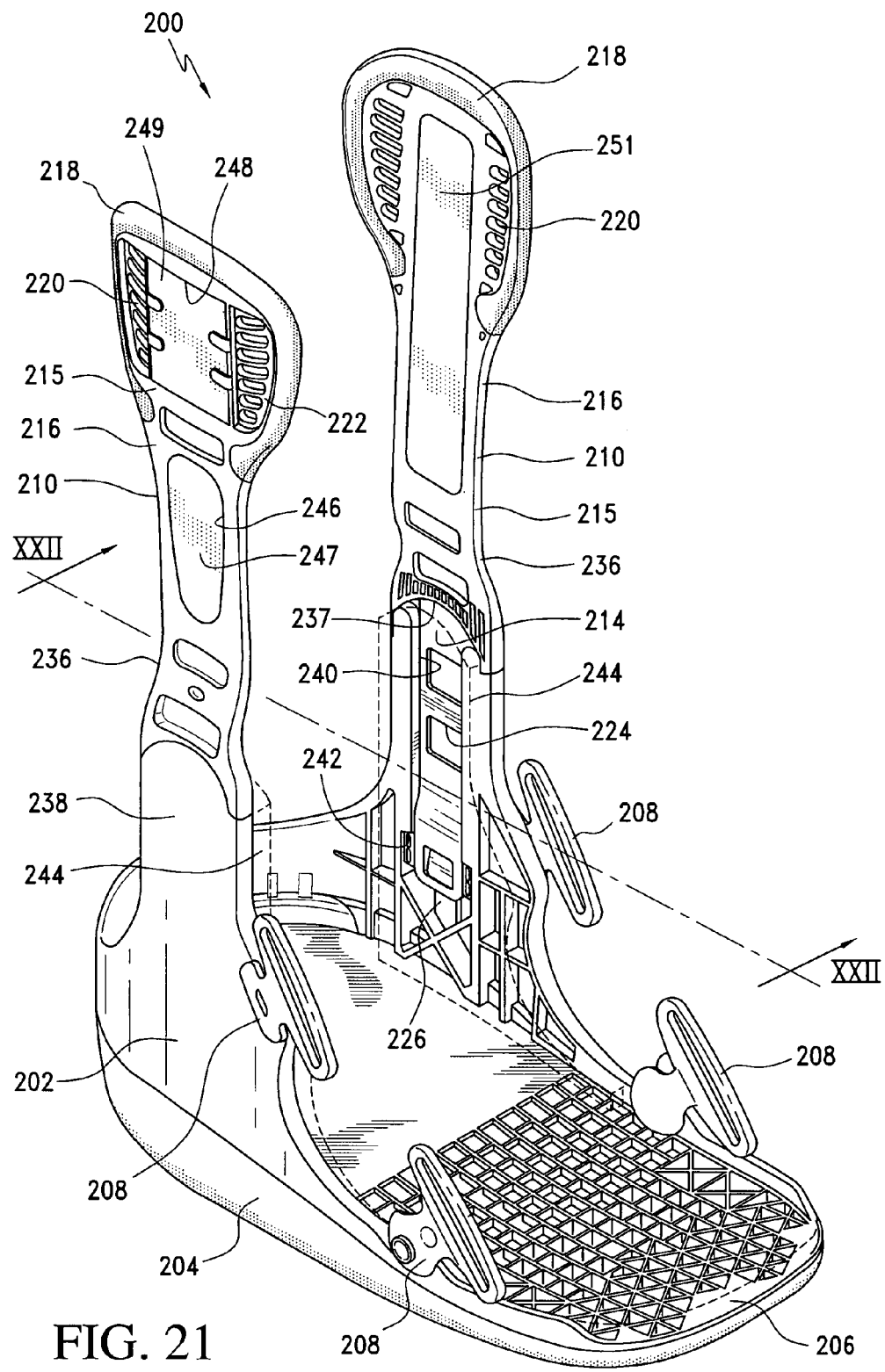
FIG. 21 is a perspective view of another embodiment an orthopedic walker.

In accordance with another embodiment of the walker, FIG. 21 exemplifies a walker 200 having struts 210 comprising frame members 214 with an over-molded supporting component 215. Within the context of this disclosure, the over-molded feature is generally defined as a feature in which one material is molded over another material or structure. The two materials are considered to be contiguous with one another. The over-molded features of these struts allow for components to have a plurality of different material properties, such as hardness, wear resistance, weight, rigidity and color, and provide for greater patient compliance, comfort and durability.

At the onset, as with other embodiments described herein, the walker 200 includes a base member 202, an outsole 204, a resilient layer 206 secured to the base member, D-rings 208, and suitable padding 244 and straps (not shown). The over-molded struts 210 can be used with any of the embodiments described herein.

Figure 22:
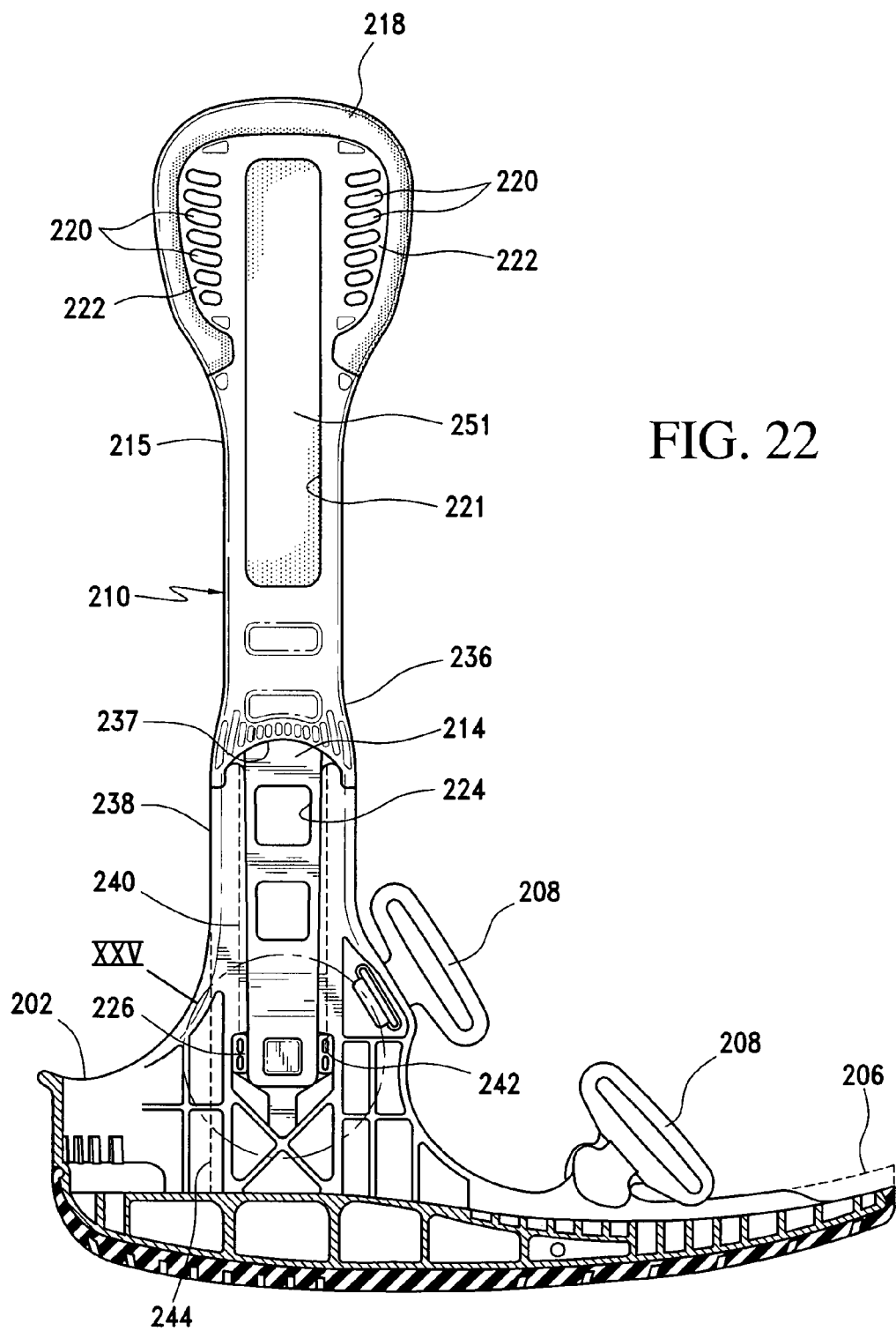
FIG. 22 is a sectional view of a first side along line XXII-XXII in FIG. 21.
Figure 23:
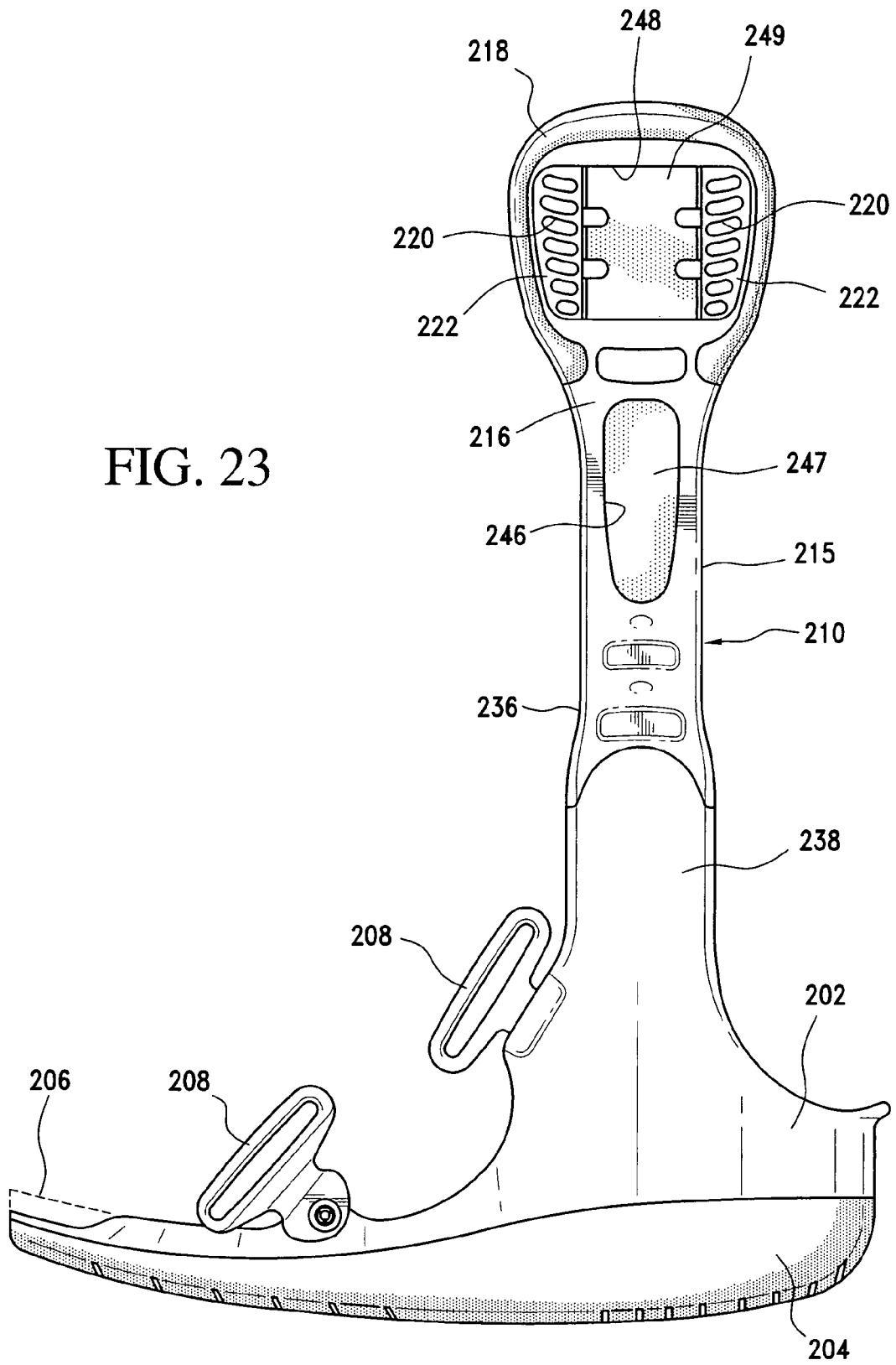
FIG. 23 is an elevational view of a second side of the sectional view shown in FIG. 22.

As illustrated in FIGS. 22 and 23, one variation of the base member 202 is provided with side strut supports 238 that extend vertically from the base member 202. The struts 210 include a locking mechanism 226 that is adapted to permanently or removably lock with the base member 202 via slots or grooves 240 and a recess 242 formed along the interior wall of the side strut support 238.

The locking mechanism 226 is provided in part so that a base member with a specified foot size may be used with struts having different lengths in order to accommodate different leg injuries at different locations of a leg or different sized leg lengths. For example, in some injuries, a low-top walker may only be necessary to secure an ankle injury. In other instances, a high-top walker may be necessary to secure the leg from a fracture below the knee. The locking mechanism allows for greater flexibility in strut sizes for the walkers, and reduces the size of packaging and the need for a large inventory of walkers.

In other variations, the frame member may be secured to the side strut support by fasteners (i.e., rivets or screws), snapped into corresponding grooves or slots, or adhesively bonded to the side strut support.

Figure 24:
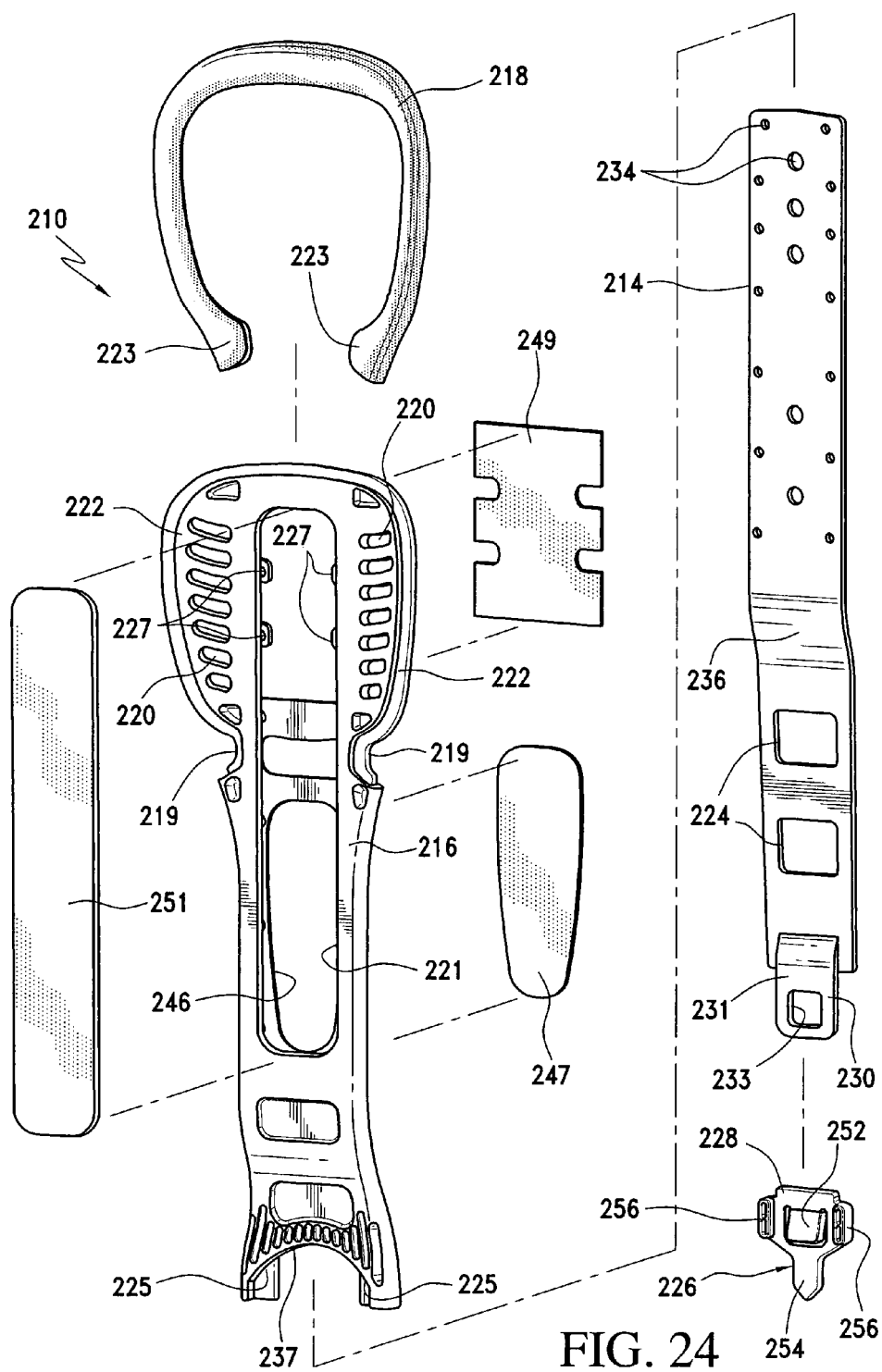
FIG. 24 is an exploded view of the strut depicted in FIG. 21.

FIG. 24 depicts one variation of the over-molded strut 210 that is adapted to be secured to the base member 202. The strut 210 includes an elongate frame member 214 comprising a high strength material and having first and second ends. The first end of the frame member 214 is arranged with a locking mechanism 226 that is configured to be secured to the base member 202. The second end of the frame member 214 includes the supporting component 215 that is configured to embrace portions of a leg, and to support supplementary features such as padding, and hook and loop material.

The frame members are preferably characterized herein as being substantially rigid. The rigidity of the frame members may result from the material from which the frame members are constructed from and/or their geometry. The material of the frame member may be selected according to strength, weight, rigidity, and malleability requirements. Exemplary materials that may be used for constructing the frame members include metal materials such as aluminum, titanium, and steel, thermoset resin composite systems including glass or carbon fibers, and thermoplastics that have been rendered rigid by way of material composition and geometry.

It will be noted that the requirement that the frame members have substantially rigid properties is provided only as an exemplary configuration. Each frame member may have flexible properties, and may further be provided in discrete segments such that the frame members are segments as opposed to being continuous. Such segments may be connected to one another by hinges, fasteners or other suitable elements.

According to one variation, the illustrated frame member 214 in the embodiments of FIGS. 21-24 is constructed from a malleable aluminum which allows for the walker to be adapted to accommodate the leg anatomy of a wearer of a particular walker. In order to accommodate the anatomy, in one variation the frame member 214 is contoured with at least one bend 236 to more closely contour the shape of a particular leg. In other variations of the frame member, the frame member is not malleable to the wearer of the brace and at least one bend is preformed to accommodate standard leg sizes.

As shown in detail in FIG. 24, the frame member 214 defines at least one opening 224 that is provided in part to reduce the weight of the frame member 214. The frame member 214 also defines a seat 230 which is located at the first end that is arranged to receive the locking mechanism 226. In addition to the opening 224, the frame member 214 defines a plurality of apertures 234 that are distinguished from the opening 224 and which are provided for permitting material of the supporting component to extend therethrough and interlock therewith, as will be discussed more fully below. For example, material extensions 227 of the supporting component 215 extend into the apertures 234, so as to effectively interlock with the frame member 214.

According to this embodiment, the frame member 214 defines a seat 230 which comprises a centrally protruding segment 231 formed from the first end of the frame member 214 and extending therefrom in a bent manner which is contoured for receiving the locking mechanism 226. The protruding segment 231 forms a slot 233 that is arranged for receiving the locking mechanism 226.

According to the variation shown in FIG. 24, the locking mechanism 226 defines a body 228 having a central tab or button 252 that is adapted to removably secure with the slot 233. The body 228 further defines an insertion point 254 and shoulders 256 that border the protruding segment 231 when the button 252 is secured thereon. The point 254 and the shoulders 256 prevent any shift of the locking mechanism 226 relative to the frame member 214.

Figure 25:
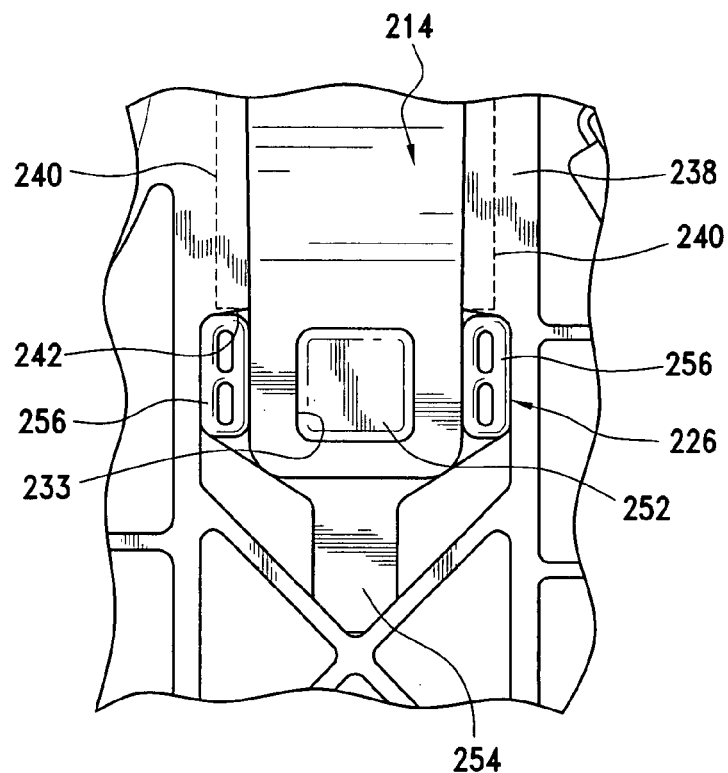
FIG. 25 is a sectional view of the locking mechanism taken from section XXV in FIG. 21.

In reference to FIGS. 22 and 25, the base member 202 defines a recess 242 located on an inside wall which accommodates the locking mechanism 226. The locking mechanism 226 is configured to securely fit within the confines and be retained within the recess 242 without any movement. The recess 242 is also formed to permit extension of the first end of the frame member 214 to slide along the grooves 240 into the recess 242 so as to secure to the locking mechanism 226.

The combination of the frame member with the locking mechanism is advantageous in that it requires minimal machining and shaping of the frame member. Instead, the locking mechanism, which is preferably molded from plastic or composite material, bears more complicated shaping over the frame member. The configuration of the locking mechanism further allows for the ease of attaching the frame member to the base member, and selective removal via the button on the locking mechanism.

In another variation of the frame member and locking mechanism, the seat may be replaced with an opening that is adapted to receive a fastener. The strut is therefore retained by the slots or grooves, and secured to the base member via a fastener such as a rivet or screw in such variations.

As mentioned above, the strut 210 further comprises the supporting component 215 that is secured to the frame member 214. The material of the supporting component 215 and the frame member may interlock at least in part via the apertures 234 and the extensions 227, and/or due to shrinkage stresses of the supporting component 215 against the frame member 214.

In a variation, the supporting component may be frictionally secured to the frame member, with or without interlocking. Alternatively, in other variations, the supporting component may also be additionally or wholly secured to the frame member via adhesive or mechanical means in a manner that would be generally understood to one skilled in the art.

In a preferred embodiment, the supporting component is less rigid than the frame member in that it is generally more compliant against the leg of the wearer of the walker. The supporting component also prevents hard or sharp surfaces that may lead to a deterioration of the soft-good support upon repeated use of the walker.

The supporting component 215 includes a plurality of openings 220 that form a ventilation feature to enable circulation of air therethrough. Ventilated padding may be used in combination with these openings 220 to allow for greater comfort to the patient. An exemplary padding is described in U.S. application Ser. No. 11/723,604 entitled "Spacer Element for Prosthetic and Orthotic Devices."

The supporting component 215 also defines a plurality of slots 221 that are arranged for receiving padding, or hook and loop material to reduce their profile along the frame members 214, and to effectively retain the material over an extended period of usage so as to improve durability. For example, slot 246 may be arranged to receive a loop-type material 247, whereas slot 248 may be arranged to receive a hook-type material 249. Likewise, slot 221 may be adapted to receive a hook-type material 251. The hook and loop material may be selected on the basis of the types of items it is arranged to attach to (i.e., straps, padding or softgood-type padding as in 42 in FIG. 1). The supporting component 215 also defines a recess 237, by way of example, wherein portions of the padding material 244 may be received therein.

According to the embodiment exemplified in FIG. 24, the supporting component 215 defines laterally extending side wings 222 that are located at or near the second end of the frame member 214. The side wings 222 may assume a variety of different shapes, and are arranged for providing greater surface contact along the leg. This allows, in part, a greater distribution of forces against the leg so as to relieve pressure exerted by the straps over the injured or infirm leg. Furthermore, by configuring the side wings as large support surfaces, the side wings may be designed to conform to patient anatomy around the circumference of the lower leg, thus increasing the functionality of the walker without solely relying on strapping to hold the leg in place. Suitable locking devices, such as buckles or removable fasteners, may be used to hold the circumferentially side wings in place against the leg.

In accordance the preferred embodiment, the supporting component is constructed from a material that is less rigid than the material of the frame member. However, in variations the supporting component may be constructed from rigid, flexible or semi-rigid material. According to one variation, the supporting component is a rigid or semi-rigid plastic; preferably the material is a polypropylene and is directly molded onto the frame member by injection molding. By injection molding the plastic of the supporting component onto the frame member, there is no need for mechanical fasteners or adhesives since the plastic contracts and interlocks against the frame member and consequently secures therewith.

FIG. 24 depicts the supporting component 215 as comprising a main body 216, and a pressure-relieving perimeter or border portion 218. The border portion 218 preferably is constructed from a material having a hardness that is lower than the hardness of the main body. Whereas the main body 216 is preferably constructed from a rigid or semi-rigid material, the border portion 218 is formed from a plastic softer than the material forming the main body. The border portion 218 thereby forms a compliant portion that relieves pressure exerted on the leg by the straps.

In this embodiment, the main body 216 and the border portion 218 are preferably injection molded thermoplastics that are integrally molded together. In making and securing the supporting component onto the member, the main body is first fabricated by being formed by a first mold that surrounds at least a portion of the member. A first material, such as polypropylene, is injected into the mold so as to result in the formation of the main body. The molded main body is then transferred to another, larger second mold which forms the shape of the definitive supporting component including the border edge portion. The main body is then secured in the second mold. A second material, such as a thermoplastic elastomer (TPE), is injected into the second mold so as to contact the main body and form the perimeter edge portion. Due to the polymeric nature of the first and second materials, the second material of the border portion integrally bonds to the first material of the main body as it is formed in the second mold.

In order to assist the interlocking of the main body with the border portion, the main body 216 defines peripheral recesses 219 that allow for the injection molded material of the border portion 218 to engage. The border portion 218 in turn defines prongs 223 with engage the recesses 219 so as to interlock with the main body 216. The ridge 219 is used to increase the soft overmold bonding surface along the edge of the supporting component 215.

A variation of the main body does not define the ridge. It may not be necessary to provide a ridge to allow for bonding of the soft overmold to the main body. Alternatively, it may be desirable to provide a thicker soft overmold which is achieved when no ridge is defined on the main body.

Within the context of this embodiment of the disclosure, the main body and the overmolded border portion are considered to be contiguous with one another. In other words, these two overmolded features are preferably secured to one another without any intermediate adhesive or fastener, and the structure of the main body and the border portion are continuous with one another. The same applies to the main body which is overmolded onto the frame member. Again, the main body is considered to be contiguous with the frame member since it directly touches the frame member. Moreover, the main body may be effectively interlocked with the frame member via the openings formed on the frame member. Because the main body is molded over the frame member, slots 225 are formed on the main body 216 which are directly adjacent the frame member 214.

It will be understood that in variations of the embodiment of FIG. 24, the main body may comprise a material that can frictionally engage onto the frame member, whether or not the main body interlocks frame member. In other variations, the shrinkage forces of the main body can at least in part retain the main body onto the frame member. In yet other variations, the main body may be mechanically adhered to the frame member, and formed separately from the frame member. Further, the border portion may be secured to the main body by adhesives and formed separately from the main body.

Numerous combinations of materials may be used to form the supporting component with our without the border portion. For example, polyethylene, polyurethane and other thermoplastics may be used for forming the main body, and suitable materials such as vinyl, rubber or thermoplastic elastomer may be used for forming the border or perimeter edge portion. Other methods for forming the main body with the perimeter edge portion. Other methods for forming the main body with the border portion may be found in U.S. Pat. Nos. 5,445,602 and 5,716,335, incorporated herein by reference. Moreover, a soft flexible border portion may be mechanically adhered, such as an adhesive, to a main body formed with a ledge, slotted or groove portions upon which the perimeter edge portion may be adhered so as not to interlock with any structure of the main body. The border portion may be formed by foamed materials or materials that have frictional properties that can grip the leg or clothing of the wearer of the walker.

The main body may be formed from a resilient material that while not as rigid as the frame member, it can yield to the patient's leg. Of course, while the main body may be resilient, it is preferable that it has a greater hardness than the border portion if included with the supporting component. Further, the supporting component may be formed solely with a main body that is either rigid or semi-rigid, without any distinction of a different hardness along the border portion.

In a variation of the supporting component, the border portion may be formed so as to form flexible or stretchable linkages and extend over a greater portion of the leg than is shown by the embodiment of FIG. 21. Opposing sides of the border portion may be secured to one another to thereby substantially extend circumferentially about the leg. This particular variation is advantageous in that circumferential walkers are generally understood as being limited by sizing since circumferential surfaces cannot conform to anatomy as well as two struts (as shown in FIG. 21). The softer and substantially resilient border portion can form linkages that flex, stretch and compress so as to allow for the surfaces to spread apart when necessary.

Figure 26:
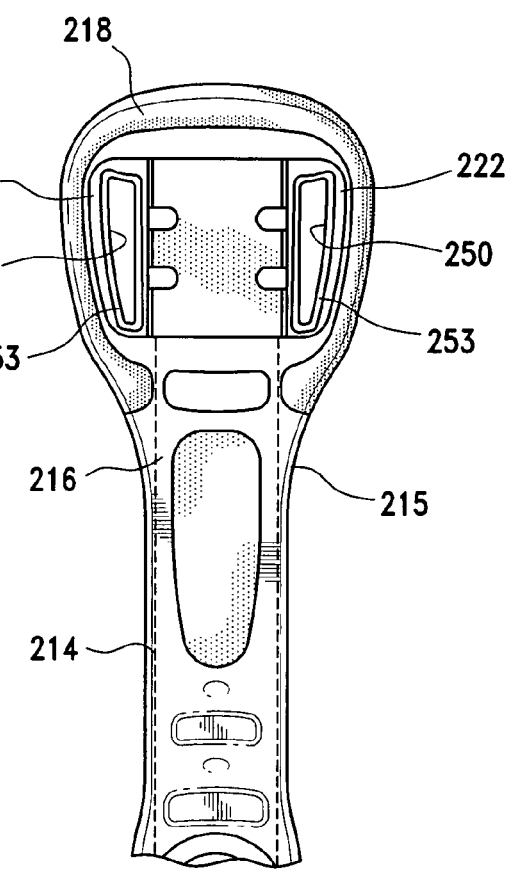
FIG. 26 is another embodiment of the strut depicted in FIG. 21.

In referring to FIG. 26, the supporting component 215 may define slots 250 which extend generally parallel to the frame member 214. The slot 250 is formed on the main body 216 in order to accommodate a strap. The slot 250 may have a discrete rim portion 253 that is molded over the slot 250 in much the same manner as the border portion in FIG. 24.

According to one variation, the rim portion 253 is generally formed on the main body 216 in a manner similar to the border portion 218. The rim portion 253 may have a hardness that is greater than the main body, a composition more durable than the main body, or having frictional nature greater than the main body. The rim portion 253 is provided at least in part in order to reduce wear on the main body due to tightening of the straps over the leg.

It will be noted that in variations of the main body, the slots may be formed on the main body without the aforementioned overmolded rim.

Unlike in conventional walkers, at least the border portion of the supporting component yields to the shape of the leg. This leads to a significant advantage in that the supporting component (i.e., the combination of soft border portion and the more rigid main body) creates a soft interface for the patient's leg. By increasing comfort it follows that patients will be more willing to wear the walker and the walker will be more effective in servings as a tool to assist in healing. Further, as compared to the substantially more rigid frame member, the softer border portion and areas of the main body with the border portion will wear easier against the softgood padding of the walker since there will be no hard edges.

Another advantage to the overmolded supporting component results in eliminating the need to configure the strut in a manner that would include portions for receiving the perimeter edge portion. As such, the main body may be molded with a perimeter edge portion that does not include ledges, slots or grooves for receiving the subsequently molded second material forming the definitive perimeter edge portion. This provides a generally continuous structure without gaps, raised areas, sharp edges and other protuberances or recesses that may cause discomfort to the wearer of the brace or may lead to a deterioration of the softgood support.

Another advantage to the supporting component having both the main body and border portion is that the border portion, being continuous with the main body, may be pigmented in a different color from main body. This results in an appearance that results of a piping around the periphery of the supporting component which provides a visually pleasing appearance. For example, the first material used for forming the main body of the sub-shell may have a black pigment, whereas the second material used for forming the perimeter edge portion may have a gray pigment.

Yet another advantage to the supporting component is that it is preferably formed by at least one plastic that is lighter than frame member. Further, the supporting component minimizes the need to machine the frame member since it effectively forms an outer shell with components molded therein. Such molded components include openings allowing for ventilation, strap slots and living hinges. Hence, the supporting component affords for greater flexibility in fabricating the walker over conventional methods that employ a strut generally formed from a single material or composite system.

In closing, it is noted that specific illustrative embodiments of the invention have been shown in the drawings and described in detail hereinabove. It is to be understood that various changes and modifications may be made without departing from the spirit and scope of the invention. Thus, by way of example and not of limitation, the locations of the rib 72 and the recess 74 may be reversed with the rib on the base and the recess on the periphery of the outsole. Also, the outer prongs on the locking mechanism may be made thinner to fit into the grooves or slots on the strut supports of the base.

In another area, the stop for reducing strut flexibility be included in the junction between the struts and the base, with one of the two mating stop surfaces being on the base, and the other stop surface being on the strut, and with the strut-to-base joint being somewhat flexible. Further, the outsole may be more permanently affixed to the walker base by overmolding the bottom of the base with the outsole, and having the outsole interlock into openings or recesses in the base. Also, the struts, either long or short, may be provided with slots, or integrally molded outwardly extending D-ring type structures for receiving straps. Accordingly the present invention is not limited to the specific embodiments shown in the drawings, or described in detail hereinabove.

The invention claimed is:

1. An orthopedic device, comprising:
   a base having first and second sides;
   at least one strut connected to the base and including:
      a frame member formed from a higher strength material and having first and second ends, the first end of the frame member secured to the first side of the base; and
      a supporting component integrally secured to and contiguous with the frame member, and defining a laterally extending side wing generally corresponding to the second end of the frame member, the supporting component being constructed from a material less rigid than the higher strength material of the frame member;
   wherein the supporting component defines area of reduced thickness for permitting low resistance flexing of the supporting component, the reduced thickness areas forming living hinges extend substantially vertically to permit flexing of the side wings relatives to the strut.

2. The orthopedic device according to claim 1, wherein the supporting component defines a pair of side wings having slots located on opposite sides of the frame member.

3. The orthopedic device according to claim 2, wherein the supporting component defines areas of reduced thickness for permitting low resistance flexing of the supporting component, the reduced thickness areas forming living hinges which extend substantially vertically to permit flexing of the side wings relative to the strut.

4. The orthopedic device according to claim 1, wherein the supporting component comprises first and second types of slots, the first set of slots located on opposite sides of the frame member and being generally parallel therewith.

5. The orthopedic device according to claim 1, wherein the supporting component defines a border portion generally located along at least a segment of a peripheral edge of the supporting component, and a main body contiguous with the frame member, the border portion having lower hardness properties than the main body.

6. The orthopedic device according to claim 5, wherein the border portion is formed from a substantially resilient plastic.

7. The orthopedic device according to claim 5, wherein the main body is formed from a substantially rigid plastic.

8. The orthopedic device according to claim 1, wherein the supporting component comprises first and second discrete and continuous materials, the first material having different hardness properties than the second material, the first material forming at least a portion of a peripheral edge of the supporting component and the second material forming at least a portion of the supporting component contiguous to the frame member.

9. The orthopedic device according to claim 1, further comprising a locking mechanism adapted for being retained by the base, and configured to secure to the frame member.

10. The orthopedic device according to claim 1, wherein the supporting component defines discrete areas having different hardness properties.

11. The orthopedic device according to claim 1, wherein the frame member is formed from a malleable aluminum.

12. An orthopedic walker for mounting on the lower leg of a patient, comprising:
   a base having a central area for receiving the foot of a patient and a spaced lower surface including an outer sole;
   at least one strut connected to the base including:
      a frame member formed from a higher strength material and having first and second ends, the first end of the frame member secured to the first side of the base; and
      a supporting component integrally secured to and contiguous to the frame member, and defining laterally extending side wings generally corresponding to the second end of the frame member, the supporting component being constructed from a material less rigid than the higher strength material of the frame member;
   the base further including a side strut support having an inner substantially vertically extending slot for receiving the strut;
   wherein the supporting component defines discrete areas having different hardness properties.

13. The orthopedic device according to claim 12, further comprising a locking mechanism arranged for securing the strut to the base, the locking mechanism defining a button for securing to the first end of the frame member, and shoulders for securing to the base.

14. The orthopedic device according to claim 12, wherein the supporting component defines a border portion generally located along at least a segment of a peripheral edge of the supporting component, and a main body generally adjacent to the frame member, the border portion having lower hardness properties than the main body and being contiguous with the main body.

15. The orthopedic device according to claim 12, wherein the supporting component defines areas of reduced thickness for permitting low resistance flexing of the supporting component, the reduced thickness areas forming living hinges which extend substantially vertically to permit flexing of the side wings relative to the strut.

16. A bracing component, comprising:
an elongate metal frame member formed from a malleable material and defining at least one opening; and
a plastic supporting component molded over and integrally secured to the frame member so as to be contiguous and continuous therewith, at least one plastic material extension belonging to the supporting component interlocking with the opening of the frame member, the supporting component having a side wing portion laterally extending at least outwardly from a length of the frame member and which defines at least one through-slot arranged generally parallel to the length of the frame member; and
at least one strap arranged to secure to and pass through the through-slot and extend from the supporting component.

17. The bracing component according to claim 16, wherein the supporting component has first and second areas each defining different hardness properties, the first area defined by a substantially rigid plastic and located adjacent the metal member, and the second area defined by a resilient plastic bordering and outer lying the first area.

18. The bracing component according to claim 17, wherein the second area is molded over portions of the first area so as to be integrally secured and contiguous therewith.

19. The bracing component according to claim 16, wherein the supporting component defines areas of reduced thickness for permitting low resistance flexing of the supporting component, the reduced thickness areas forming living hinges which permit flexing portions of the supporting component relative to the frame member.

20. The bracing component according to claim 16, wherein the frame member is formed from aluminum.

21. The bracing component according to claim 16, further comprising a padding material, wherein the supporting component defines at least one recess adapted to receive the padding material.

22. The bracing component according to claim 16, wherein the supporting component covers peripheral edge of the frame member.

23. A bracing component, comprising:
a rigid frame member defining at least one opening, the frame member having longitudinal edges defines along a longitudinal length thereof; and
a rigid or semi-rigid plastic supporting component molded over and integrally secured to the frame member, at least one plastic material extension belonging to the supporting component interlocking with the opening plastic material extension belonging to the therewith, the supporting component surrounding and protruding at least laterally from the longitudinal edge defined along a segment of the longitudinal length of the frame member;
wherein the supporting component is constructed from a material less rigid that a material forming the frame member.

\* \* \* \* \*